US012520898B2

(12) United States Patent
Caron et al.

(10) Patent No.: US 12,520,898 B2
(45) Date of Patent: Jan. 13, 2026

(54) PROTECTIVE HELMET

(71) Applicant: ABUS August Bremicker Söhne KG, Wetter-Volmarstein (DE)

(72) Inventors: Jean-Francois Caron, Berlin (DE); Stefan Richert, Berlin (DE)

(73) Assignee: ABUS August Bremicker Söhne KG, Wetter-Volmarstein (DE)

( * ) Notice: Subject to any disclaimer, the term of this patent is extended or adjusted under 35 U.S.C. 154(b) by 0 days.

(21) Appl. No.: 18/779,383

(22) Filed: Jul. 22, 2024

(65) Prior Publication Data

US 2025/0049163 A1 Feb. 13, 2025

(30) Foreign Application Priority Data

Aug. 8, 2023 (DE) ......................... 102023121097.1

(51) Int. Cl.
*A42B 3/06* (2006.01)
*A61F 9/02* (2006.01)

(52) U.S. Cl.
CPC .............. *A42B 3/062* (2013.01); *A61F 9/022* (2013.01)

(58) Field of Classification Search
CPC ............ A42B 3/223; A42B 3/22; A42B 3/221
See application file for complete search history.

(56) References Cited

U.S. PATENT DOCUMENTS

| | | | | |
|---|---|---|---|---|
| 6,301,721 | B1 * | 10/2001 | Arai | A42B 3/222 2/424 |
| 2003/0051289 | A1 | 3/2003 | Gafforio et al. | |
| 2016/0015114 | A1 * | 1/2016 | Berthier | A42B 3/222 2/424 |
| 2018/0242677 | A1 * | 8/2018 | Pilenga | A42B 3/20 |
| 2019/0357624 | A1 * | 11/2019 | Rietzler | A42B 3/185 |
| 2025/0000195 | A1 * | 1/2025 | Rogers | A42B 3/223 |

FOREIGN PATENT DOCUMENTS

| | | | |
|---|---|---|---|
| DE | 3441078 | A1 | 3/1986 |
| EP | 3970545 | A1 | 3/2022 |
| FR | 2541874 | A1 | 9/1984 |
| FR | 2637468 | A1 | 4/1990 |

* cited by examiner

*Primary Examiner* — Katherine M Moran
(74) *Attorney, Agent, or Firm* — Dickinson Wright PLLC

(57) ABSTRACT

In a protective helmet, in particular a sports helmet, with a shock-absorbing helmet shell and a visor, on each of two opposite sides of the protective helmet, a coupling section of the helmet shell and a coupling section of the visor are formed, one of which is configured as a coupling receptacle and the other as a coupling extension and in such a way that, the coupling extension may engage in the coupling receptacle in order to connect the visor to the helmet shell. The coupling extension is displaceable in the coupling receptacle along a displacement path between an initial position and an advance position and is pivotable about a pivot axis between the advance position and an open position.

16 Claims, 4 Drawing Sheets

PROTECTIVE HELMET

CROSS-REFERENCE TO RELATED APPLICATION

This application claims the benefit and priority of German Patent Application No. 102023121097.1 filed on Aug. 8, 2023. The entire disclosure of the above application is incorporated herein by reference.

FIELD OF THE INVENTION

The invention relates generally to a protective helmet, in particular to a sports helmet, having a shock-absorbing helmet shell and a visor.

BACKGROUND OF THE INVENTION

Protective helmets may be expedient for various types of activities in order to protect the head of the respective helmet wearer. In particular, this may involve sporting activities such as cycling. In this case, the protective helmet may be configured as a sports helmet.

A protective helmet usually comprises a helmet shell that can be placed on the head of the respective helmet wearer and is shock-absorbing, so that an impact against the head may be absorbed and at least attenuated by the protective helmet. In this way, the risk of injury to the helmet wearer caused by such an impact may be reduced. For example, the helmet shell may comprise a thin outer shell made of a hard material and a substantially thicker helmet body comprising a deformable, in particular foamed, material, or is formed from this. It is desirable for the helmet shell to cover large parts of the head when the helmet is put on, in particular if it extends at least from the forehead to the neck and sideways to the temples and around the ears.

It may also be desirable to protect the area around the eyes, whether it's mechanically against impacts or the ingress of objects such as dust or pollen, or optically against excessive sunlight. This function may not usually be fulfilled by the helmet shell itself, as this is usually opaque and would also be too thick. However, a protective helmet may comprise a visor to protect the region around the eyes, which may protect the eyes mechanically and also optically, for example by means of an appropriate tint.

Fundamentally, such a visor may be rigidly mounted to the helmet shell. However, it is often preferable if the visor can be adjusted between a closed position, in which it covers the eye region of the head of the respective helmet wearer when the helmet is put on, and an open position, in which it is opened (typically upwards in front of the forehead or even further). Additionally, it is advantageous if the visor may be completely detached from the helmet shell in a simple manner and likewise attached to it again in a simple manner. In this way, a protective helmet user may selectively mount the visor to the helmet shell or not, as required. However, it should be ensured that the manner in which the visor is mounted to the helmet shell is such that an unintentional detachment of the visor during the respective activity may be ruled out with sufficient reliability.

Conventional protective helmets having a folding visor typically have comparatively large hinge mechanisms. If it is provided for at all, that the visor may be completely detached from the helmet shell in a simple manner, at least a part of the respective hinge mechanism usually remains on the helmet shell after detachment, where it then takes up excessive space and is visually perceived as disturbing.

SUMMARY OF THE INVENTION

It is an object of the invention to provide a protective helmet, in particular a sports helmet, having a visor mounted to a helmet shell of the protective helmet by means of a reliable mechanism which may be configured in a particularly compact manner and integrated in the protective helmet in a particularly inconspicuous manner, while allowing the visor to be adjusted between an open position and a closed position, and ideally also allowing the visor to be attached to the helmet shell of the protective helmet as required in a particularly simple manner or to be completely detached from the helmet shell. This object is achieved by a protective helmet having the features of claim 1. Advantageous embodiments of the invention may be taken from the dependent claims, the present description and the figures.

The protective helmet according to the invention comprises a shock-absorbing helmet shell and a visor. In particular, the helmet shell may be configured to be placed on the head of a helmet wearer. For this purpose, the helmet shell may have at least approximately a hemispherical shape. In particular, the visor may be configured to be positioned in front of the eyes of the respective helmet wearer. Preferably, the visor is at least partially transparent.

The protective helmet may have an upper side as well as a front side, a rear side, a first and second side which adjoin the upper side, wherein the front side and the rear side are oriented opposite to one another and wherein the first side and the second side are also oriented opposite to one another and respectively adjoin both the front side and the rear side. The front side may be oriented to face at least substantially the line of vision of a respective helmet wearer and cover the forehead of the respective helmet wearer when the protective helmet is put on the wearer's head in a manner intended for this purpose, while the rear side is oriented to face the opposite direction and with the protective helmet on, covers the back of the head of the helmet wearer. The first side and the second side may each be oriented to face at least substantially perpendicular to these directions. The helmet shell may also have an upper side, a front side, a rear side, a first side and a second side, which correspond to said upper side, front side, rear side, first side and second side of the protective helmet.

The visor may be connected to the helmet shell at the first side and at the second side of the protective helmet. The visor may have at least substantially the shape of a radially outwardly pointing surface of a spherical carving (i.e. an elongated curved shape with a width decreasing towards the ends of its longitudinal extent, in particular with tapered ends). In a closed position, the visor may extend from the first side to the second side, in particular along said front side of the protective helmet. In an open position, on the other hand, the visor may extend in particular along a transition from the front side to the upper side of the protective helmet or along the upper side of the protective helmet from the first side to the second side.

According to the invention, a coupling section of the helmet shell and a coupling section of the visor are formed on each of two opposite sides of the protective helmet. These two opposite sides of the protective helmet may in particular be said first side and said second side of the protective helmet, which correspond to a first side and a second side of the helmet shell, respectively. The visor may be connected to the helmet shell by the interaction of the respective coupling section of the helmet shell with the respective coupling section of the visor on both sides of the protective helmet.

On both said sides of the protective helmet, one of the two coupling sections formed on the respective side (namely, the coupling section of the helmet shell formed on the respective side and the coupling section of the visor formed on the respective side) is formed as a coupling receptacle and the other as a coupling extension. Preferably, the coupling sections formed on the helmet shell are each configured as a coupling receptacle, while the coupling sections formed on the visor are configured as a coupling extension. Insofar as a respective coupling receptacle is formed on the helmet shell, it is preferably configured as a recess in said helmet body of the helmet shell.

The coupling receptacle and the coupling extension as well as their interaction are described in more detail below. The term coupling receptacle or coupling extension is mostly used in the singular. Since a coupling section configured as a coupling receptacle (of the helmet shell or visor) and a coupling section configured as a coupling extension (of the respective other part) are provided on both said sides of the protective helmet, and despite the singular, the description is not to be understood as limited to the one coupling receptacle or the one coupling extension (on one of the two sides); rather, both the coupling receptacle on one side and the coupling receptacle on the other side of the protective helmet or both the coupling extension on one side and the coupling extension on the other side of the protective helmet may be configured in the described manner in each case. Preferably, the two coupling sections on one side of the protective helmet and the two coupling sections on the other side of the protective helmet are configured in a corresponding manner to each other, in particular to be mirror images of each other.

According to the invention, the coupling receptacle and the coupling extension are configured such that the coupling extension may engage in the coupling receptacle in order to couple the visor to the helmet shell. In other words, the coupling between the visor and the helmet shell is achieved at least in part by the coupling extension engaging in the coupling receptacle. The direction of engagement, i.e. the direction of engagement of the coupling extension in the coupling receptacle, may in particular be oriented radially (inwards or outwards) with respect to a center point of the helmet shell (in particular a center point of said hemispherical-like shape of the helmet shell). Said coupling, on the one hand, may serve to mount the visor to the helmet shell, but it may also serve to moveably mount the visor to the helmet shell. Furthermore, the coupling is preferably reversible (i.e. intended to be detachable) so that the visor may selectively be mounted on the helmet shell or, if it is not needed, may be omitted.

Furthermore, according to the invention it is provided for, that the coupling extension in the coupling receptacle, i.e. when it engages in the coupling receptacle, is displaceable along a displacement path between an initial position and an advance position and is pivotable about a pivot axis between the advance position and an open position. In other words, the coupling receptacle and the coupling extension may be configured relative to one another in such a way that the coupling extension is displaceable in the coupling receptacle along the displacement path between the initial position and the advance position and is pivotable about a pivot axis between the advance position and the open position.

The coupling extension may thus assume said initial position, said advance position and said open position, whereby the coupling extension is located in the coupling receptacle in each of these positions. In addition, the coupling extension may be displaced from the initial position along said displacement path into the advance position and pivoted from the advance position about said pivot axis into the open position and, conversely, pivoted from the open position about said pivot axis into the advance position and displaced from the advance position along said displacement path into the initial position. The coupling extension is also located in the respective coupling receptacle during these movements (displacing and pivoting).

In particular, the coupling receptacle and the coupling extension may be configured in such a way that a movement of the coupling extension from the initial position into the open position or from the open position into the initial position inevitably takes place via the advance position. Furthermore, it is advantageous if the initial position and the open position are opposite end positions of the movement of the coupling extension within the coupling receptacle, beyond which (in the direction going away from the respective opposite end position) the coupling extension may not be moved within the coupling receptacle. From the initial position, however, the coupling extension may also be removable from the coupling receptacle (opposite to said direction of engagement).

The designations of the three positions (initial position, advance position and open position) primarily serve to conceptually differentiate these positions from one another. Fundamentally, these positions could also be referred to as the first position, second position or third position. The coupling extension is expediently rigidly connected to the visor or to the helmet shell (depending on whether it is constructed at the visor or at the helmet shell), so that the positions correspond to corresponding positions of the visor relative to the helmet shell. In particular, the initial position of the coupling extension may correspond to a closed position of the visor and the open position of the coupling extension may correspond to an open position of the visor.

In some embodiments, the respective coupling extension and the associated coupling receptacle may be configured such that the coupling extension can only be pivoted in the advance position, but not in the initial position or along the displacement path. This simplifies for the user an intuitive, haptically guided handling of the visor.

In some embodiments, the respective coupling extension and the associated coupling receptacle may be configured such that the coupling extension can only be moved along the displacement path, but not in other directions, starting from the initial position in relation to a plane that extends transversely to said direction of engagement and includes the displacement path. This also simplifies for the user an intuitive, haptically guided handling of the visor.

Said displacement path along which the coupling extension can be moved between the initial position and the advance position is preferably at least substantially rectilinear. In other words, a moving of the coupling extension in the coupling receptacle along the displacement path is at least substantially a pure translation. It may be useful if, starting from the initial position, the displacement path initially comprises an exact straight section (a pure translation), which however is followed by a slightly angled and/or slightly curved pre-pivot section that extends to the advance position, or if the displacement path as a whole is configured as a slightly curved pre-pivot section. Such a pre-pivot section (as a type of sloped ramp) may support and thus facilitate the transition between a displacement of the coupling extension along the displacement path and a pivoting of the coupling extension about the pivot axis in the region of the advance position.

The rotational component of the movement of the coupling extension along the displacement path resulting from such a pre-pivot section is preferably relatively small compared to the translational component. For example, the movement of the coupling extension along the displacement path may have a rotational component of at most 10°, preferably at most 5°. In contrast, the movement of the coupling extension along the displacement path preferably has a translational component of at least 10 mm, preferably at least 12 mm.

Furthermore, it is preferable if the pivot axis, about which the coupling extension can pivot between the advance position and the open position, is oriented at least substantially perpendicular to the displacement path. If the displacement path is not exactly rectilinear, the pivot axis is preferably oriented perpendicular to a plane within which the displacement path runs. Independent of this, fundamentally it is preferable if the pivot axis is oriented parallel to said direction of engagement in which the coupling extension engages in the coupling receptacle. In this respect, the displacement path or said plane within which it runs is preferably oriented perpendicular to the direction of engagement.

The pivoting of the coupling extension between the advance position and the open position is preferably a pure rotation. However, this pivoting movement may fundamentally also have a comparatively small translational component. Preferably, this translational component is at most 2 mm, in particular at most 1 mm. On the other hand, the rotational component of the pivoting movement between the advance position and the open position is preferably at least 25°, in particular at least 30°.

By coupling the visor to the helmet shell via the described engagement of a respective coupling extension in a respective coupling receptacle taking place on both sides of the protective helmet, the visor may be reliably mounted to the helmet shell and is adjustable between different positions (in particular between said closed position and said open position). In addition, this coupling may be configured to be especially compact and largely inconspicuously integrated in the helmet shell. This applies in particular when the coupling receptacles are each formed in the helmet shell, for example, as a recess in the helmet body into which a respective coupling extension formed on the visor engages.

According to an advantageous embodiment, the coupling receptacle comprises a displacement section which has at least substantially the shape of an elongated hole, and a pivoting section which has at least substantially the shape of a circular sector. The displacement section may lead into the pivoting section. The displacement section and the pivoting section may also overlap. Preferably, the displacement section and the pivoting section together form the coupling receptacle. Preferably, the coupling extension is located at least substantially within the displacement section during a displacement between the initial position and the advance position along the displacement path. During pivoting between the advance position and the open position about the pivot axis, the coupling extension, on the other hand, is preferably located at least substantially within the pivoting section.

The described shapes of the displacement section and the pivoting section may each be related in particular to a cross-section perpendicular to said direction of engagement and/or to the pivot axis. Parallel to the direction of engagement or to the pivot axis, this cross-section of the displacement section or of the pivoting section is preferably at least substantially constant.

The displacement section may have the shape of an elongated hole in particular in that it has an elongated shape which extends along the displacement path and has an at least substantially constant width perpendicular to the pathway of the displacement path (as well as perpendicular to the direction of engagement and/or to the pivot axis), i.e. is bound by two edges at a constant distance.

In particular, the pivoting section may have the shape of a circular sector insofar as this shape is bound in the radial direction with respect to the pivot axis by a circular arc and in the rotational direction about the pivot axis by a circular radius in each case (i.e. in the two pivoting directions in which the coupling extension can be pivoted between the advance position and the open position). One of the two circular radii is preferably oriented at least substantially in the extent of one of said edges of the displacement section, in particular parallel to this edge. However, it may also be configured as a sloped ramp by being slightly curved or slightly angled relative to said edge. In particular, this can result in said pre-pivot section of the displacement path.

Depending on the shape of the coupling extension and/or the type of connection of the coupling extension to the rest of the visor or to the rest of the helmet shell, the coupling receptacle may also comprise two pivoting sections, each of which has at least substantially the shape of a circular sector. With regard to the pivot axis, these two pivoting sections may then be arranged in particular diametrically opposed to each other, so that together they form a butterfly shape.

According to a further advantageous embodiment, the coupling extension comprises a base section having an elongated shape which extends along a longitudinal axis and which is completely received in the coupling receptacle in the initial position, the advance position and in the open position, as well as comprising a connecting section which extends along a transverse axis oriented transverse, in particular perpendicular, to the longitudinal axis and connects the base section to the rest of the visor or to the rest of the helmet shell (depending on whether the coupling extension is formed on the visor or on the helmet shell). Preferably, the base section and the connecting section together form the coupling extension.

The described shape of the base section may in particular be related to a cross-section perpendicular to the direction of engagement and/or to the pivot axis. The cross-section of the base section parallel to the direction of engagement or to the pivot axis is preferably at least substantially constant.

In particular, the base section may comprise an elongated shape insofar as it has its greatest extent (at least in cross-section) along said longitudinal axis and in the direction(s) perpendicular thereto extends significantly less far, in particular at most half as far. For example, the elongated shape in cross-section may be formed by two diametrically opposed semicircles spaced apart from each other, which are connected to each other at their ends by two mutually parallel lines.

In particular, the connecting section may have a cylindrical shape. The transverse axis along which the connecting section connects the base section to the rest of the visor or to the rest of the helmet shell may then correspond to the cylindrical axis of this cylindrical shape. In particular, the coupling extension may engage in the coupling receptacle parallel to this transverse axis. In this respect, the transverse axis is then parallel to said direction of engagement. The coupling extension may engage in the coupling receptacle to such an extent that the base section is completely received in the coupling receptacle, whereas the connecting section (in all three said positions of the coupling extension and preferably also in all intermediate positions) extends from the base section out of the coupling receptacle in the direction opposite to the direction of engagement towards the rest of the visor or the rest of the helmet shell.

Preferably, the base section is rigidly connected to the connecting section and the connecting section is rigidly connected to the rest of the visor or to the rest of the helmet shell, so that overall the entire coupling extension is rigidly formed at the visor or at the helmet shell. As a result, moving or pivoting the coupling extension inevitably corresponds to a corresponding movement or pivoting of the visor or the helmet shell at which the coupling extension is formed.

The described embodiments of the coupling receptacle and the coupling extension allow in particular, that in the initial position of the coupling extension, its base section, with its longitudinal axis oriented parallel to the displacement path, is arranged at an end of the displacement section of the coupling receptacle that is distanced from the pivoting section in the coupling receptacle. The coupling extension may then be moved within the displacement section, at least substantially parallel to its longitudinal axis, along the displacement path and up to an opposite end of the displacement section where the displacement section leads into the pivoting section or overlaps with it, so that the coupling extension then assumes the advance position.

In the advance position, the base section of the coupling extension may then be pivoted within the pivoting section of the coupling receptacle. Preferably, the coupling extension is pivoted about the transverse axis of its connecting section, which in this respect coincides with the pivot axis. In doing so, the base section may traverse the circular sector shape of the pivoting section from the one said circular radius to the other said circular radius, which may limit the pivoting section in the direction of rotation about the pivot axis. Ultimately after pivoting, the coupling extension then assumes the open position. In the opposite direction, the movement from the open position via the advance position into the initial position may take place the other way around.

Due to the described embodiment of the base section and the connecting section, the base section may be oriented in particular radially with respect to said transverse axis along which axis the connecting section extends. Depending on where along the longitudinal axis of the base section the connecting section is connected to the base section, the base section may extend from the transverse axis of the connecting section in only one radial direction or however in two opposite radial directions.

For example, the connecting section may be connected to the base section at one end of the extent of the base section along the longitudinal axis (i.e. at one of two ends between which the base section extends along the longitudinal axis). Preferably, the connecting section is only connected to the base section at this one end. Alternatively, however, the connecting section may also be connected to the base section in a central area of the extent of the base section along the longitudinal axis, in particular exactly in the middle of this longitudinal extent.

According to a further advantageous embodiment, the coupling extension is positively guided when moving between the initial position and the advance position and/or when pivoting between the advance position and the open position. In particular, this can mean that the respective movement of the coupling extension within the coupling receptacle has exactly only one degree of freedom. The restriction to the one degree of freedom may result in particular from a direct, preferably at least partially guided, interaction between the coupling extension and the coupling receptacle.

According to a further advantageous embodiment, a guide structure is formed at the coupling receptacle which interacts with a guide structure formed at the coupling extension, and in such a way that the coupling extension is guided along the displacement path when being moved between the initial position and the advance position. The guiding of the coupling extension may result in particular from the fact that said guide structures slide along each other, thereby directing a movement of the coupling extension along a certain path, in particular the displacement path.

For reliable guidance, the guide structures may advantageously interlock. For example, the guide structures may be configured in the form of a tongue-and-groove connection, i.e. on the one hand they may have at least one groove, and at least one tongue (in the sense of a ridge) that engages in the groove on the other. The guide then results in particular from the sliding of the tongue in the groove.

The guide structure of the coupling extension may be formed in particular at said base section of the coupling extension, preferably at at least one edge of the base section pointing in a direction perpendicular to the longitudinal axis and to the transverse axis. Preferably, a respective part of the guide structure is formed at two opposite such edges of the base section.

The guide structure of the coupling receptacle may be formed in particular at the displacement section of the coupling receptacle, preferably at at least one edge of the displacement section which limits the coupling receptacle transverse to the direction of engagement. Preferably, a respective part of the guide structure is formed at two opposing such edges of the displacement section.

Furthermore, it is preferred that the guide structure formed at the coupling receptacle and the guide structure formed at the coupling extension each comprise a guide bar, and the guide bar of the coupling extension engages behind the guide bar of the coupling receptacle in such a way that the coupling extension is positively secured against leaving the coupling receptacle along the displacement path (i.e. against movement out of the coupling receptacle, in particular against the direction of engagement). The guide bar may be formed respectively by a freely protruding bar or also by the edge of a groove. In particular, it is important for the positive securing that an undercut is made by the guide bar formed at the coupling receptacle, which may be engaged from behind by the guide bar formed at the coupling extension.

According to a further advantageous embodiment, the coupling extension may be secured in the coupling receptacle by a positive fit (in particular by engaging behind parts of the coupling receptacle) against leaving the coupling receptacle, counter to said direction of engagement, as soon as the coupling extension has been moved from the initial position along the displacement path. This allows the visor to be particularly reliably secured to the helmet shell as soon as the user has moved the visor out of the initial position. In some embodiments, in the initial position the visor may be secured by other measures to prevent it from unintentionally leaving the coupling receptacle counter to the direction of engagement, for example by a magnetic force-fit or by a mechanical force-fit (in particular by latching).

In particular, the coupling extension may be positively secured against leaving the coupling receptacle in the advance position, in the open position, along the displacement path and between the advance position and the open position (the latter refers to all positions that are passed through when pivoting between the advance position and the open position). In particular, it is preferable for the coupling extension to leave the coupling receptacle at least substantially exclusively in the initial position. In all other positions within the coupling receptacle, the coupling extension is preferably positively secured against leaving the coupling receptacle.

Along the displacement path, the coupling extension may be positively secured in the coupling receptacle by said guide bars, for example. In addition and/or in the other positions, the coupling extension may be positively secured in the coupling receptacle, for example, by an outer shell of the helmet shell or a cover shell arranged thereon which extends at least partially over the coupling receptacle, for example in that at least a part of said base section engages behind an edge of this outer shell or cover shell.

In order to enable simple detachment of the visor from the helmet shell, it is advantageous if the coupling extension may fundamentally leave the coupling receptacle in the initial position, in particular by simply being able to be pulled out of the coupling receptacle against the direction of engagement in the initial position. Conversely, for easy attachment of the visor to the helmet shell, it is useful if the coupling extension may be inserted simply into the coupling receptacle in the direction of engagement such that it then assumes the initial position. For reliable coupling of the visor to the helmet shell, it is important that the coupling extension is also secured in the initial position in the coupling receptacle, so that if possible it only leaves it when it is intentionally released.

For example, the coupling extension may be pretensioned in the coupling receptacle due to the visor's inherent elasticity. Such inherent elasticity may, for example, pretension said ends of the visor from the outside against the helmet shell. In the initial position, the coupling extension may then be secured in the coupling receptacle due to the pretension, but nevertheless may be easily removed from the coupling receptacle, in particular by simply pulling in the opposite direction to overcome the pretension.

For a particularly reliable coupling of the visor to the helmet shell, the coupling extension in the initial position may be secured in the coupling receptacle by magnetic means as an alternative to said pretensioning or (preferably) in addition to it.

According to a further advantageous embodiment, the coupling receptacle and the coupling extension each comprise a magnetic element, wherein the magnetic elements, namely the magnetic element of the coupling receptacle and the magnetic element of the coupling extension, are arranged in such a way that the coupling extension is held in the initial position by a magnetic force-fit (i.e. the attraction acting between the two magnetic elements). In other words, this magnetic force-fit must be overcome in order to move the coupling extension away from the initial position, in particular to move it so far away that it is not pulled back again into the initial position by the magnetic attraction.

In particular, the magnetic force-fit must be overcome in order to remove the coupling extension from the coupling receptacle against the direction of engagement (in order to detach the visor from the helmet shell). However, it may also be necessary to overcome the magnetic force-fit in order to move the coupling extension from the initial position into the advance position. Said magnetic elements may be configured (in particular, arranged relative to each other) in such a way that, against the direction of engagement a greater force must be applied to overcome the magnetic force-fit than in the direction along the displacement path towards the advance position.

For example, said base section of the coupling extension or also the coupling extension as a whole may be ferromagnetic and thus form the magnetic element. Alternatively, a ferromagnetic element or also a permanent magnet may be arranged in or at the coupling extension, in particular in or at its base section. In a corresponding manner, a ferromagnetic element or also a permanent magnet may be arranged at the coupling receptacle, in particular in the vicinity of the area of the coupling receptacle in which the coupling extension is located in its initial position.

According to a further advantageous embodiment, a support recess is formed at one edge of the coupling receptacle for supporting the coupling extension when pivoting between the advance position and the open position. In particular, the support recess may (also) be formed in a guide bar formed at said edge. When being pivoted, the coupling extension may be supported at the support recess particularly with said base section, preferably with an end of the extent of the base section along its longitudinal axis, in particular with that end connecting said connecting section to the base section. The coupling extension may be supported at the support recess insofar as it at least partially engages in it (in particular, necessarily) when pivoting between the advance position and the open position and slides along it.

According to a further advantageous embodiment, the coupling receptacle and the coupling extension are configured such that the coupling extension is fixed in the open position by latching. In other words, when pivoting from the advance position into the open position, the coupling extension latches into place in the open position. To leave the open position, i.e. to pivot from the open position into the advance position, this latching connection must be overcome again by an appropriate force. In this way, the visor is held in its open position and is thus secured against closing on its own.

According to a further advantageous embodiment, the coupling receptacle comprises a resilient latching projection which the coupling extension passes when pivoting between the advance position and the open position and which is temporarily pushed back by the coupling extension (when passing). Said latching may occur just through this interaction of the coupling extension with the latching projection. In particular, the latching projection may only be passed by the coupling extension if it is pushed back by the coupling extension. The force required to push it back thus corresponds to the force required to overcome the latching connection.

The latching projection may, for example, be arranged in such a way that it may be pushed back by the base section of the coupling extension, in particular by an end of the extent of the base section along said longitudinal axis which is oriented pointing radially away from said transverse axis. The latching projection may, for example, be formed at an edge of the coupling receptacle, in particular formed integrally with this edge. Preferably, the latching projection is formed in said pivoting section, in particular at said circular arc of the circular sector shape of the pivoting section.

Alternatively or in addition to securing by latching, the coupling extension may also be secured magnetically in the open position. For this purpose, the coupling receptacle and the coupling extension may each comprise a magnetic element, which are arranged in an appropriate manner.

According to a further advantageous embodiment, the helmet shell comprises a shield which, when the coupling extensions are in their initial position, is adjacent the visor in the direction of rotation with respect to the pivot axis and projects radially beyond the visor (i.e. in a direction which is at least substantially radial with respect to the pivot axis and thus transverse, but not necessarily exactly perpendicular, to the direction of rotation about the pivot axis).

When the coupling extensions are in their initial position, the visor assumes its closed position. Due to the fact that the shield protrudes beyond the visor in said manner when the visor is closed, the visor in the closed position may not simply be opened directly about the pivot axis and past the shield (if the coupling receptacles and coupling extensions fundamentally would allow this). Rather, it is necessary for the visor to first be moved at least substantially in the direction in which the shield protrudes so that it can be opened past the shield.

Accordingly, in this embodiment it is further provided for, that when the coupling extensions are in the advance position, the open position or in-between (and the visor is thus offset in said manner), the visor is arranged radially beyond the shield and distanced from the pivot axis. In particular, this may mean that the visor is further away from any point on the pivot axis in the radial direction to the pivot axis than the shield. In this offset position, the visor may then be pivoted past the shield in the direction of rotation about the pivot axis into its open position. In this way, the possibility of selectively mounting a visor to the helmet shell, and the provision of a shield on the helmet shell are not mutually exclusive, despite a comparatively close-fitting arrangement of the visor to the helmet shell.

DRAWINGS

The invention is explained further below merely by way of example with reference to the figures.

DESCRIPTION OF THE INVENTION

Figure 1:
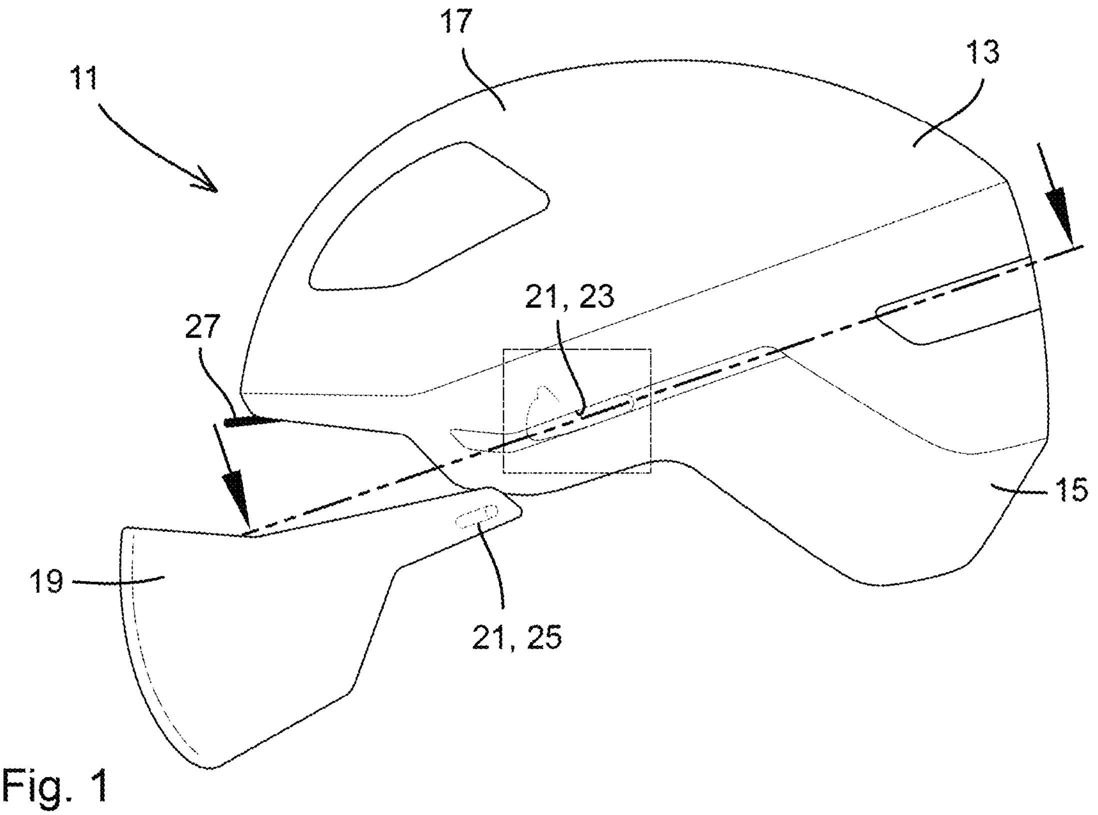
FIGS. 1 to 4 show an embodiment of a protective helmet according to the invention in four different visor positions of the protective helmet.

In the figures, an embodiment of a protective helmet 11 according to the invention is respectively shown in simplified form. In each of FIGS. 1 to 4, the protective helmet 11 is shown entirely from one viewing direction, namely from the side. FIGS. 5 to 9, on the other hand, each show only a section of the protective helmet 11 from several different viewing directions.

The protective helmet 11 shown is a sports helmet, namely a bicycle helmet. The protective helmet 11 comprises a shock-absorbing helmet shell 13 having an at least substantially hemispherical-shape, a helmet body 15 and a thin outer shell 17. The helmet body 15 may comprise, for example, foamed polystyrene as the material, and the outer shell 17 may comprise, for example, an acrylonitrile-butadiene-styrene copolymer as the material. The protective helmet 11 further comprises a visor 19 having an elongated curved shape with at least substantially tapered ends. The visor 19 is at least partially formed from a transparent material.

On a side of the protective helmet 11 facing the viewer in FIGS. 1 to 4, a coupling section 21 is formed at the helmet shell 13. Another similar coupling section 21 is also formed at the helmet shell 13 on the opposite side of the protective helmet 11 facing away from the viewer and is therefore not visible in the figures. Furthermore, the visor 19 also comprises a coupling section 21 at each of its two opposite ends, wherein only the coupling section 21 formed at the end facing the viewer is shown in the figures due to the viewing direction. The coupling section 21 is shown by a dotted-line, as it is formed on the inside of the visor 19 facing away from the viewer.

The coupling sections 21 formed at the helmet shell 13 are each configured as a coupling receptacle 23 in the form of a recess formed in the helmet body 15. On the other hand, the coupling sections 21 formed at the visor 19 are formed as coupling extensions 25 projecting from the remaining visor 19.

In FIG. 1, the visor 19 is shown in a state detached from the helmet shell 13. However, the visor 19 may be coupled to the helmet shell 13 as required by inserting the coupling extension 25 formed at the visor 19 into the coupling receptacle 23 formed at the helmet shell 13 on both sides of the protective helmet 11. The coupling extension 25 thereby engages in the coupling receptacle 23 in each case in a direction of engagement which is oriented at least substantially perpendicular to an outside of the helmet shell 13 in the region of the respective coupling receptacle 23 or oriented at least substantially facing towards a center point of the hemispherical-shaped helmet shell 13.

Fundamentally, it could also be the other way round where the coupling sections 21 formed at the helmet shell 13 are each configured as coupling receptacles 23 and the coupling sections 21 formed at the visor 19 are each configured as coupling extensions 25, whereby the direction of engagement would be oriented in the opposite direction.

In order to attach the visor 19, it may be necessary to expand the visor 19 against the inherent elasticity of the visor 19, i.e. to deflect its ends away from each other in the direction counter to said inherent elasticity of the visor 19. The restoring force resulting from the inherent elasticity then pretensions the coupling extensions 25 in the respective coupling receptacle 23, so that the engagement of the coupling extensions 25 in the coupling receptacles 23 is supported and the coupling extensions 25 are then held in the respective coupling receptacle 23 by the pretension. The coupling extensions 25 may also be magnetically secured in the coupling receptacles 23, as will be explained further below.

Figure 2:
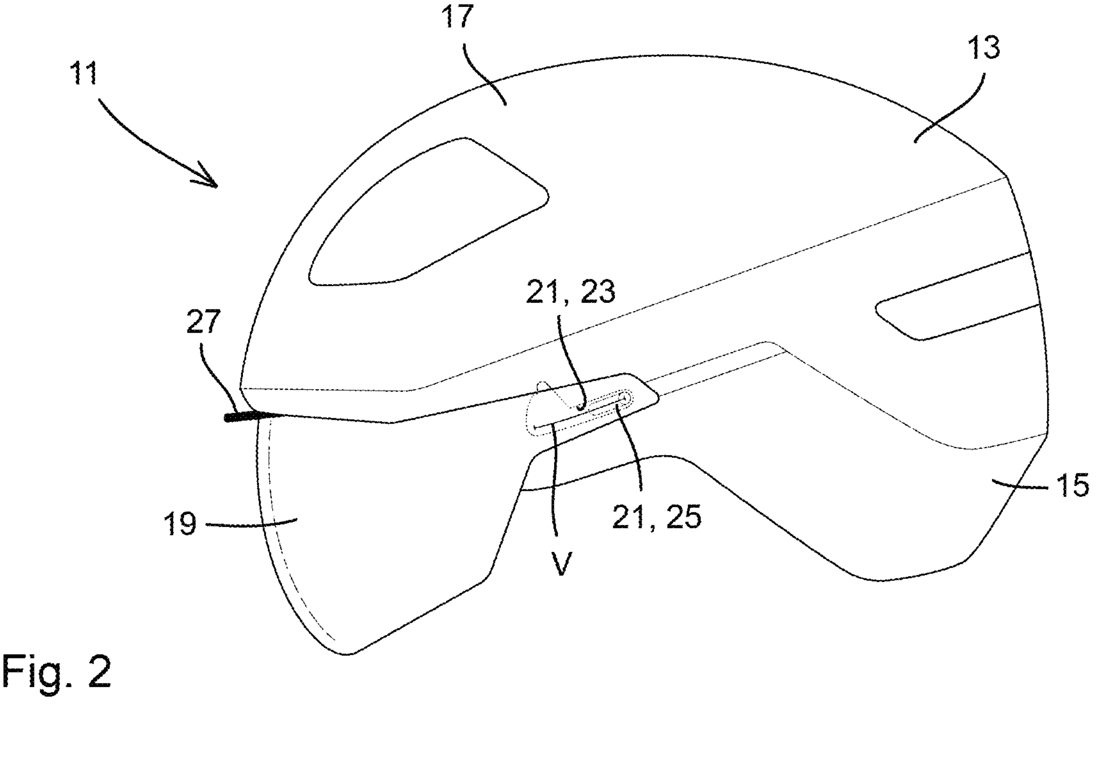
Figure 3:
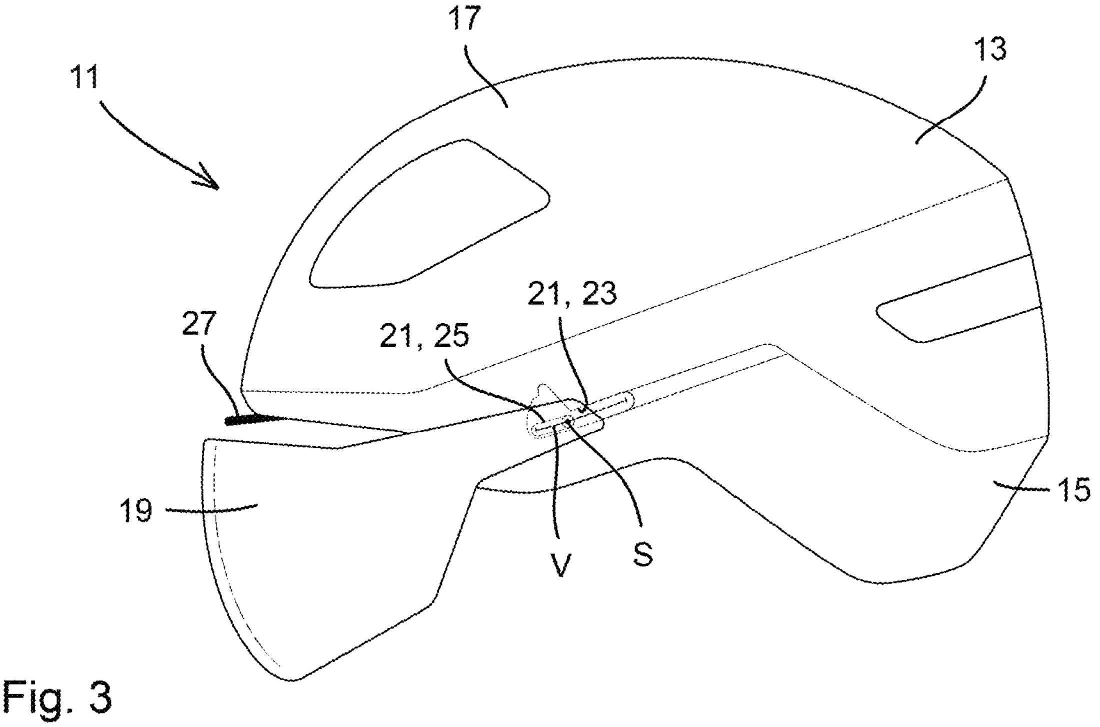
Figure 4:
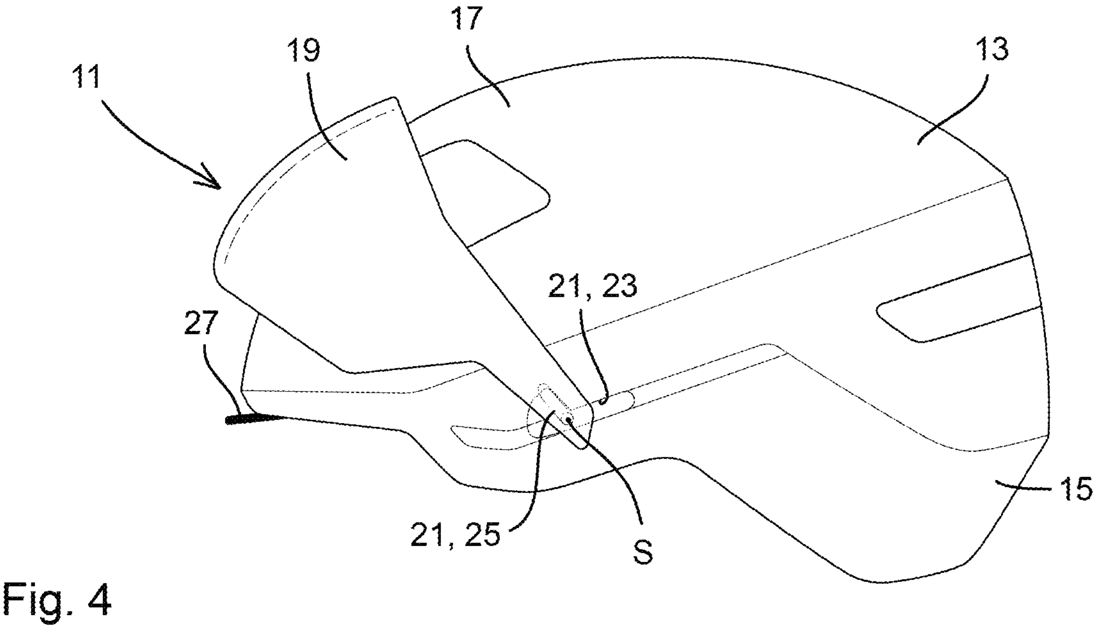

Within the respective coupling receptacle 23, the respective coupling extension 25 may assume different positions, namely, in particular the initial position shown in FIG. 2, the advance position shown in FIG. 3 and the open position shown in FIG. 4. The coupling receptacle 23 and the coupling extension 25 are configured relative to each other such that the coupling extension 25 can be displaced within the coupling receptacle 23 from the initial position along an at least substantially rectilinear displacement path V (see FIGS. 2 and 3) into the advance position, and can be pivoted about a pivot axis S which is perpendicular to the displacement path V (see FIGS. 3 and 4) and pivoted out of the advance position into the open position and, conversely, can be pivoted from the open position about the pivot axis S into the advance position and can be displaced from the advance position along the displacement path V into the initial position.

This mobility of the coupling extension 25 in the coupling receptacle 23 from the initial position via the advance position into the open position and back from the open position via the advance position into the initial position is at least substantially positively guided, i.e. limited to a single degree of freedom. In other words, the coupling extension 25 may be displaced between the initial position and the advance position at least substantially exclusively along the sliding path V, and may be pivoted between the advance position and the open position at least substantially exclusively about the pivot axis S. Furthermore, the coupling receptacle 23 and the coupling extension 25 are configured relative to one another in such a way that, from said positions, the coupling extension 25 when inserted into the coupling receptacle 23 inevitably assumes as first the initial position and, conversely, may also be removed from the coupling receptacle 23 at least substantially exclusively in the initial position.

Since the coupling extensions 25 are rigidly connected to the rest of the visor 19, the visor 19 assumes a position relative to the helmet shell 13 which corresponds to the respective position of the coupling extensions 25 within the respective coupling receptacle 23. When the coupling extensions 25 assume the initial position, the visor 19 is in the closed position shown in FIG. 2; when the coupling extensions 25 are displaced into the advance position, the visor 19 is correspondingly moved into the position shown in FIG. 3; and when the coupling extensions 25 are in the open position, the visor 19 assumes the open position shown in FIG. 4.

In the embodiment shown, the protective helmet 11 comprises a shield 27 arranged at the helmet shell 13 and projects from the helmet shell 13 at a front side of the protective helmet 11. The visor 19 in the direction of rotation about the pivot axis S adjoins the shield 27 in its closed position. If, on the other hand, the visor 19 is pushed forward, the visor 19 is further away from the pivot axis S than the shield 27, so that the visor 19 may be pivoted past the shield 27 from the position shown in FIG. 3 into the open position shown in FIG. 4. This type of adjustment of the visor 19 therefore makes it possible to provide both a shield 27 and a visor 19 on the protective helmet 11 and still make the protective helmet 11 compact.

The adjustability of the visor 19 is based on the described movability of the coupling extensions 25 in the coupling receptacles 23, which arises in particular from the respective shape of these coupling sections 21. The specific design of the coupling receptacles 23 and the coupling extensions 25 can be understood in particular from FIGS. 5 to 9 which show in detail one of the coupling receptacles 23 included in the marked region of FIG. 1, and also the coupling extension 25 (with the exception of FIG. 5) interacting with this coupling receptacle 23.

Figure 5:
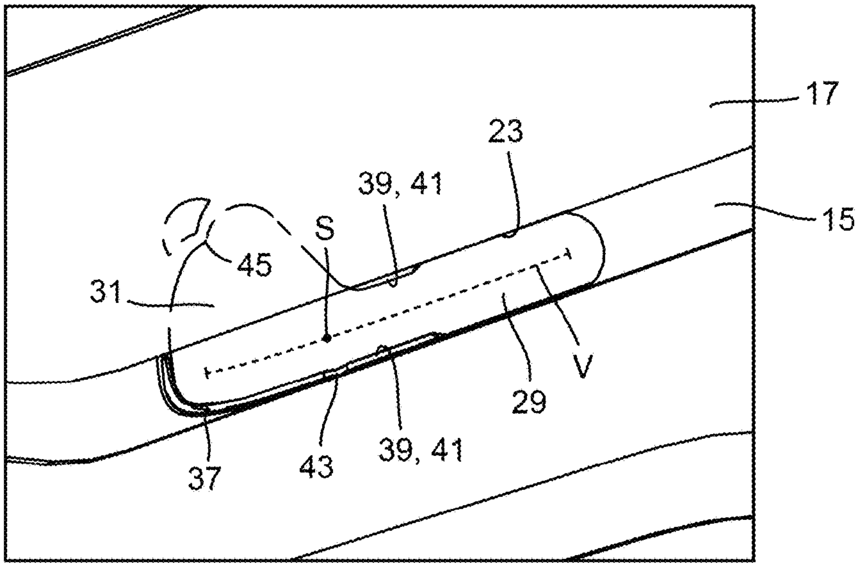
FIGS. 5 to 9 show detailed illustrations of a coupling section of a helmet shell of the protective helmet and a coupling section of the visor interacting with it.
Figure 6:
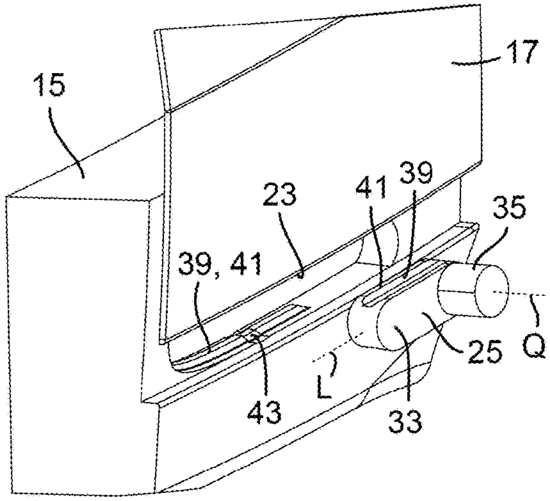
Figure 7:
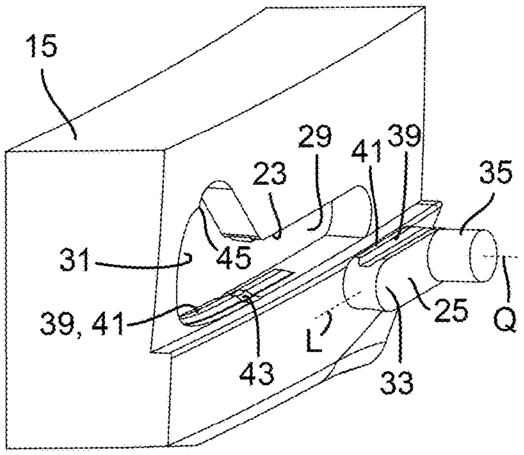

The coupling receptacle 23 comprises a displacement section 29, which has at least substantially the shape of an elongated hole, and a pivoting section 31, into which the displacement section 29 leads into and which has at least substantially the shape of a circular sector (see in particular FIG. 5). The coupling extension 25 comprises a base section 33, which has an elongated shape and extends along a longitudinal axis L, and a connecting section 35, which has a cylindrical shape and extends along a transverse axis Q oriented transverse to the longitudinal axis L (see in particular FIG. 9). The connecting section 35 is connected to the base section 33 at one end of the extent of the base section 33 along the longitudinal axis L.

In the initial position, in the advance position and during movement along the displacement path, the coupling extension 25 is oriented with the longitudinal axis L of its base section 33 to be at least substantially parallel to the displacement path V. The cylindrical axis of the cylindrical shape of the connecting section 35 coincides with the pivot axis S in the advance position and in the open position as well as in the intermediate positions of the coupling extension 25, and the coupling extension 25 can pivot about the pivot axis S between the advance position and the open position.

Transverse to the displacement path V, the displacement section 29 of the coupling receptacle 23 is bound by two parallel edges opposite each other, one of which transitions in a straight extent into an edge of the pivoting section 31 and which limits the pivoting section 31 in the direction of rotation about the pivot axis S and is therefore oriented at least substantially radially with the pivot axis S. This edge of the pivoting section 31 is slightly bent towards the opposite edge of the pivoting section 31 with increasing distance from the pivot axis S and thus forms a sloped ramp 37 (see FIG. 5). As a result, when moving along the displacement path V the coupling extension 25 is already slightly pivoted in the direction of the open position shortly before reaching the advance position. The displacement path V is therefore not exactly straight, but rather due to said sloped ramp 37 has a pre-pivot section which supports the transition between the movement along the displacement path V and the pivoting about the pivot axis S.

At the edges of the coupling receptacle 23, a respective guide structure 39 is provided which is configured as a guide bar 41 that projects from the respective edge into the coupling receptacle 23 and runs parallel to the displacement path V. At mutually opposite edges of the base section 33 which limit the base section 33 transversely to its longitudinal axis L and which slide along the edges of the coupling receptacle 23 during displacement along the displacement path V, a respective guide structure 39 is also provided which is configured as a guide groove.

When the coupling extension 25 is displaced along the displacement path V, the guide bars 41 of the guide structure 39 formed on the coupling receptacle 23 engage in the respective guide groove formed on the corresponding edge of the base section 33 of the coupling extension 25 in the manner of a tongue-and-groove connection and slide along it. As a result, the coupling extension 25 is guided along the displacement path V when being displaced between the initial position and the advance position.

The edge of the respective guide groove furthest away from the connecting section 35 may also be regarded as a guide bar 41 which engages behind the corresponding guide bar 41 formed on the coupling receptacle 23 with respect to the direction of engagement when the coupling extension 25 is displaced along the displacement path V, so that the coupling extension 25 is positively secured against leaving the coupling receptacle 23 counter to the direction of engagement during displacement along the displacement path V and preferably also in the advance position due to this rear engagement.

Also when the coupling extension 25 is pivoted about the pivot axis S, when the guide bars 41 no longer engage behind each other, the coupling extension 25 is positively secured against leaving the coupling receptacle 23 counter to the direction of engagement. This is because the base section 33 of the coupling extension 25 engages behind the outer shell 17 of the helmet shell 13 of the protective helmet 11 (see FIG. 6).

Figure 8:
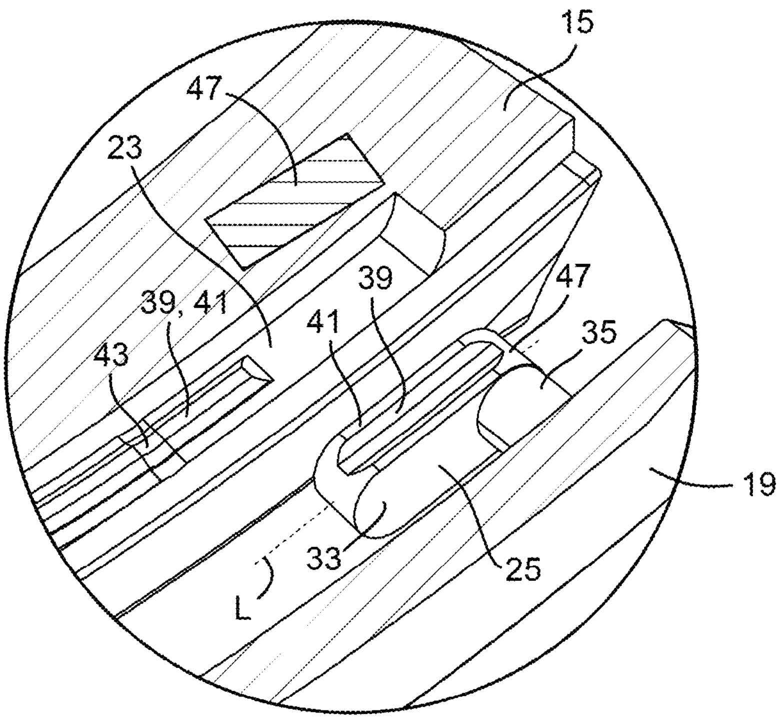
Figure 9:
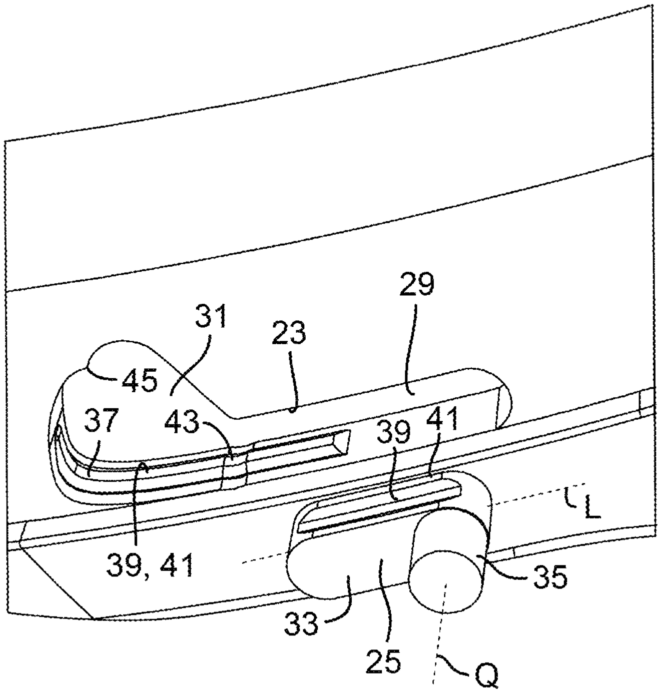

At one edge of the coupling receptacle 23, namely at the edge formed by the edges of the displacement section 29 and the pivoting section 31 of the coupling receptacle 23 which transition with one another in a straight extent, a support recess 43 is formed in a section that is closest to the pivot axis S (see in particular FIG. 8). The support recess 43 is formed in the edge as an elongated recess parallel to the pivot axis S. Since one of said guide bars 41 is also formed on this edge, the support recess 43 also extends through this guide bar 41. In other words, part of the support recess 43 is formed in this guide bar 41. The support recess 43 is arranged in such a way that the end of the longitudinal extent of the base section 33 of the coupling extension 25 through which the pivot axis S runs (since the connecting section 35 connects the base section 33 at this end to the rest of the visor 19) is supported at the support recess 43 when pivoting about the pivot axis S.

A resilient latching projection 45 is formed at a further edge of the coupling receptacle 23, which edge limits the pivoting section 31 of the coupling receptacle 23 in the radial direction relative to the pivot axis S. The latching projection 45 is arranged in such a way that the coupling extension 25 passes it, namely by the end of the longitudinal extent of the base section 33 of the coupling extension 25 that points radially away from the pivot axis S, shortly before reaching the open position and the latching projection is thereby temporarily pushed back, i.e. elastically deflected. After passing, the latching projection returns back due to its elasticity. As a result, the coupling extension 25 engages in the open position and is then held in the open position due to this latching. However, the coupling extension 25 may also be pivoted back in the opposite direction from the open position, past the latching projection 45 and back into the advance position by applying an opposing force high enough for a renewed push-back of the latching projection 45. The described latching of the coupling extension 25 into the open position secures overall the visor 19 against unintentional displacement out of the open position.

In the example shown, the latching projection 45 is formed by a section of the edge of the pivoting section 31 which has a reduced radius relative to the pivot axis S and behind which a space is provided, so that the section is thin-walled and may be elastically pushed back into the space. Fundamentally, however, the resilient latching projection 45 may also be configured in many different ways, for example as a latching tongue or latching spring projecting from the edge. The latching projection 45 may also be formed separately from the edge and mounted at a suitable position within the coupling receptacle 23. Furthermore, the latching projection 45 need not necessarily be provided at the edge, but may also be arranged, for example, at a base of the coupling receptacle 23.

The base section 33 of the coupling extension 25 includes a ferromagnetic material and thus comprises a magnetic element 47. At the end of the longitudinal extent of the displacement section 29 of the coupling receptacle 23 which is distanced from the pivoting section 31, the coupling receptacle 23 also comprises a magnetic element 47 in the form of a permanent magnet embedded in the helmet body 15 (see FIG. 8, which shows a cut-out section of the protective helmet 11 along the plane marked in FIG. 1). A magnetic attraction arises between these magnetic elements 47 which depends on their distance from each other. If the distance is sufficiently small, this results in a magnetic force-fit which pulls the coupling extension 25 into the initial position or holds it in the initial position.

In this way, the coupling extensions 25 are secured in the respective coupling receptacle 23 not only due to the inherent elasticity of the visor 19 but also additionally by the magnetic force-fit when they are in their initial position, in which they fundamentally may be removed from the respective coupling receptacle 23. Nevertheless, an intentional detachment of the visor 19 from the helmet shell 13 in an easy manner is possible by pulling the respective coupling extension 25 out of the coupling receptacle 23 with sufficient force to overcome the magnetic force-fit and to counter the pretension resulting from the inherent elasticity of the visor 19.

Due to the magnetic interaction of said magnetic elements 47, the respective coupling extension 25 is not only secured against detachment from the coupling receptacle 23, but advantageously also against being unintentionally displaced into the advance position or against any slipping. The magnetic elements 47 thus also secure the visor 19 in its closed position. By providing a further magnetic element 47 in the region of said latching projection 45 (in addition to this or in place of), the described latching of the coupling extension 25 in the open position may also take place by a magnetic force-fit, so that the visor 19 is also magnetically secured in its open position.

The described manner of coupling the visor 19 to the helmet shell 13 allows the visor 19 to be easily attached to the helmet shell 13 or left off as required, and when attached to the helmet shell 13 it may also be adjusted between a closed position and an open position without any great effort while being reliably secured to the helmet shell 13. The structures provided for coupling the visor 19 to the helmet shell 13, namely the coupling extensions 25 and the coupling receptacles 23, take up comparatively little space, so that the protective helmet 11 may have a comparatively slim design despite having these advantageous functions.

What is claimed is:

1. A protective helmet having a shock-absorbing helmet shell and a visor, wherein, on each of two opposite sides of the protective helmet, a coupling section of the helmet shell and a coupling section of the visor are formed, one of which is configured as a coupling receptacle and the other as a coupling extension such that the coupling extension is configured to engage in the coupling receptacle in order to connect the visor to the helmet shell, wherein the coupling extension is displaceable in the coupling receptacle along a displacement path between an initial position and an advance position and is pivotable about a pivot axis between the advance position and an open position;

wherein the coupling extension comprises a base section having an elongated shape which extends along a longitudinal axis and which is completely received in the coupling receptacle in the initial position, in the advance position and in the open position, and a connecting section which extends along a transverse axis oriented transverse to the longitudinal axis and connects the base section to the rest of the visor or to the rest of the helmet shell.

2. The protective helmet according to claim 1, wherein the displacement path is at least substantially rectilinear.

3. The protective helmet according to claim 1, wherein the pivot axis is oriented at least substantially perpendicular to the displacement path.

4. The protective helmet according to claim 1, wherein the coupling receptacle comprises a displacement section having at least substantially the shape of an elongated hole, and a pivoting section having at least substantially the shape of a circular sector.

5. The protective helmet according to claim 1, wherein the connecting section is connected to the base section at one end of the extent of the base section along the longitudinal axis.

6. The protective helmet according to claim 1, wherein the coupling extension is positively guided during displacement between the initial position and the advance position and/or during pivoting between the advance position and the open position.

7. The protective helmet according to claim 1, wherein a guide structure is formed at the coupling receptacle that interacts with a guide structure formed at the coupling extension in such a way that the coupling extension is guided along the displacement path during displacement between the initial position and the advance position.

8. The protective helmet according to claim 7, wherein the guide structure formed at the coupling receptacle and the guide structure formed at the coupling extension each comprise a guide bar, and the guide bar of the coupling extension engages behind the guide bar of the coupling receptacle in such a way that the coupling extension is positively secured along the displacement path against leaving the coupling receptacle.

9. The protective helmet according to claim 1, wherein the coupling extension is positively secured against leaving the coupling receptacle in the advance position, in the open position, along the displacement path and between the advance position and the open position.

10. The protective helmet according to claim 1, wherein the coupling receptacle and the coupling extension each comprise a magnetic element and the magnetic elements are arranged in such a way that the coupling extension is held in the initial position by a magnetic force-fit.

11. The protective helmet according to claim 1, wherein a support recess is formed at one edge of the coupling receptacle, and at which support recess the coupling extension is supported during pivoting between the advance position and the open position.

12. The protective helmet according to claim 1, wherein the coupling receptacle and the coupling extension are configured such that the coupling extension is secured in the open position by latching.

13. The protective helmet according to claim 1, wherein the coupling receptacle comprises a resilient latching projection which the coupling extension passes when pivoting between the advance position and the open position and in doing so temporarily pushes back.

14. The protective helmet according to claim 1, wherein the helmet shell comprises a shield which, when the coupling extensions are in their initial position, adjoins the visor in the direction of rotation with respect to the pivot axis and projects radially beyond the visor, and wherein the visor, when the coupling extensions are in the advance position, the open position or in-between, is arranged distanced from the pivot axis radially beyond the shield.

15. A protective helmet having a shock-absorbing helmet shell and a visor, wherein a coupling section of the helmet shell and a coupling section of the visor are formed on each of two opposite sides of the protective helmet, one of which is configured as a coupling receptacle and the other as a coupling extension such that the coupling extension is configured to engage in the coupling receptacle in order to connect the visor to the helmet shell, wherein the coupling extension is displaceable in the coupling receptacle along a displacement path between an initial position and an advance position and is pivotable about a pivot axis between the advance position and an open position, and wherein the coupling receptacle and the coupling extension each comprise a magnetic element and the magnetic elements are arranged in such a way that the coupling extension is held in the initial position by a magnetic force-fit.

16. A protective helmet having a shock-absorbing helmet shell and a visor, wherein, on each of two opposite sides of the protective helmet, a coupling section of the helmet shell and a coupling section of the visor are formed, one of which is configured as a coupling receptacle and the other as a coupling extension such that the coupling extension is configured to engage in the coupling receptacle in order to connect the visor to the helmet shell, wherein the coupling extension is displaceable in the coupling receptacle along a displacement path between an initial position and an advance position and is pivotable about a pivot axis between the advance position and an open position, wherein a support recess is formed at one edge of the coupling receptacle, and at which support recess the coupling extension is supported during pivoting between the advance position and the open position.

* * * * *